United States Patent [19]

Sheiban

[11] Patent Number: 5,226,889
[45] Date of Patent: Jul. 13, 1993

[54] DOUBLE BALLOON CATHETER FOR STENT IMPLANTATION

[76] Inventor: Imad Sheiban, Via Sommavalle No. 9, Verona, 37128, Italy

[21] Appl. No.: 734,968

[22] Filed: Jul. 24, 1991

[30] Foreign Application Priority Data

Jul. 30, 1990 [IT] Italy ............................ 84979 A/90

[51] Int. Cl.$^5$ ............................................. A61M 29/00
[52] U.S. Cl. ............................ 604/101; 606/194; 604/264; 623/12
[58] Field of Search ................... 604/96–103, 604/264, 265, 280, 282; 606/191, 192, 194; 623/1, 12

[56] References Cited

U.S. PATENT DOCUMENTS

| | | |
|---|---|---|
| 4,527,549 | 7/1985 | Gabbay . |
| 4,577,631 | 3/1986 | Kreamer .................... 623/12 |
| 4,723,549 | 2/1988 | Wholey et al. .............. 606/194 |
| 4,728,328 | 3/1988 | Hughes ....................... 623/12 |
| 4,733,665 | 3/1988 | Palmaz . |
| 4,744,366 | 5/1988 | Jang ........................... 604/101 |
| 4,795,458 | 1/1989 | Regan ......................... 606/194 |
| 5,002,532 | 3/1991 | Gaiser et al. ................ 606/194 |
| 5,078,726 | 1/1992 | Kreamer ..................... 606/194 |

Primary Examiner—C. Fred Rosenbaum
Assistant Examiner—Chalin Smith
Attorney, Agent, or Firm—Gerstman & Ellis, Ltd.

[57] ABSTRACT

A balloon catheter comprises a flexible catheter shaft and at least a pair of inflatable balloons carried on the shaft. Each of the balloons communicate with a separate inflation lumen extending longitudinally within the shaft. One of the pair of balloons is carried on the shaft in a position relatively proximal to the other. Typically, the relatively proximal balloon carries a stent for implantation into a patient.

11 Claims, 1 Drawing Sheet

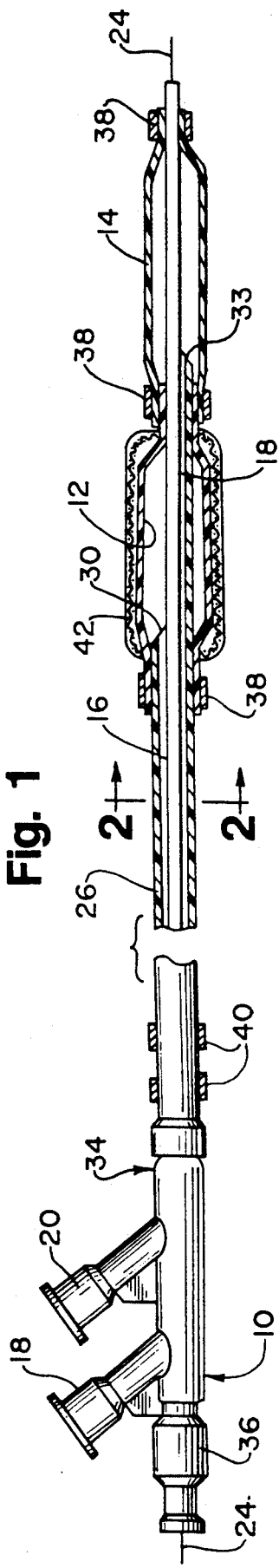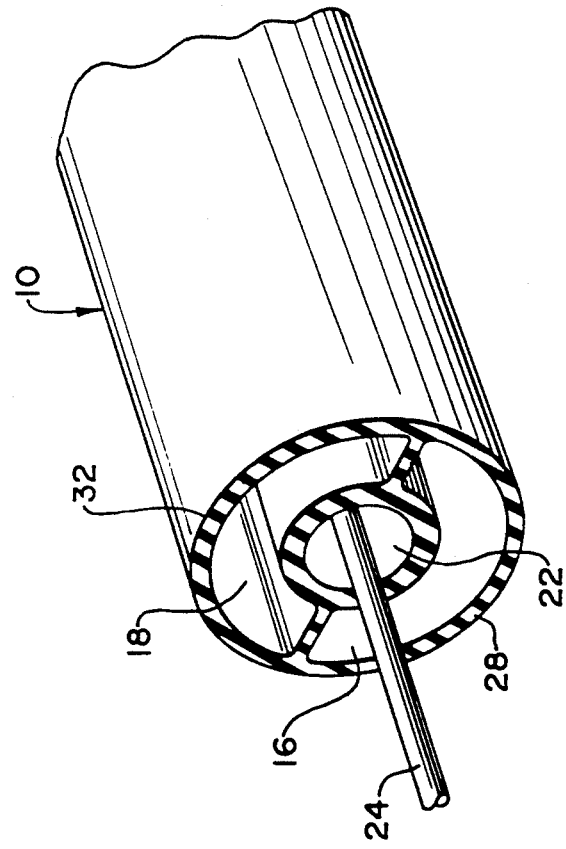

DOUBLE BALLOON CATHETER FOR STENT IMPLANTATION

BACKGROUND OF THE INVENTION

As disclosed for example by Palmaz U.S. Pat. No. 4,733,665 expandable grafts or stents may be implanted into the vascular system of a patient to prevent collapse of the lumen of a segment of a vein or particularly an artery. Such grafts or stents are typically made of tubular wire mesh which initially begin at a reduced outer diameter and are carried about an expansion balloon of an angioplasty catheter. Then, when the stent is properly positioned, the balloon is expanded to enlarge the diameter of the wire mesh stent. Once the diameter of the wire mesh stent is so enlarged, the stent is basically locked by one of a variety of known prior art techniques so that it does not collapse again after the balloon is deflated and the catheter withdrawn.

While a large variety of such stents and stent emplacement systems are known as prior art, the respective prior art systems exhibit the disadvantage that, naturally, a catheter balloon which carries a stent has a larger outer diameter than the smallest deflated angioplasty catheter balloons. Thus, particularly in the case of a very tight stenosis in an artery, it may not be possible to emplace the deflated angioplasty balloon and its carried stent into the stenosis, as would be desirable so that the stenosis may be expanded, and then the stent may be emplaced to prevent recollapse of the stenosis, for example as part of a PTCA procedure.

In such a circumstance, in the prior art it may be necessary for the surgeon to pass through the stenosis with a catheter having a relatively small dilatation balloon on a guidewire. Then, after expanding the stenosis with a small dilatation balloon, that catheter has to be withdrawn, and another catheter, having a larger dilatation balloon and carrying the stent, must be advanced to pass into the stenosis which has been partially expanded.

Such a procedure is of course inconvenient and difficult, requiring two catheters. Also, sometimes during the period between the withdrawal of the first catheter and the advancement of the second catheter the stenosis can recollapse, so that it remains impossible to get the stent and its typically larger balloon through the stenosis despite the initial expansion action of the smaller balloon of the first catheter.

The catheter of this invention addresses the disadvantages found in the prior art, providing a single catheter which is capable of penetrating very narrow, tight stenoses where only a very small lumen remains, yet which is also capable of expanding a stent to a diameter larger than the inflated diameter of the initial, small balloon which penetrates the stenosis. Thus, a double advantage is provided by the catheter of this invention, in that it is capable of penetrating very tight stenoses, but also it is capable of expanding and emplacing a stent of large enough diameter that the small balloon that initially penetrates the stenosis could not be used to expand the stent to the desired diameter.

DESCRIPTION OF THE INVENTION

By this invention, a balloon catheter is provided which comprises a flexible catheter shaft and at least a pair of inflatable balloons carried on the catheter shaft. Each of the balloons communicates with a separate inflation lumen extending longitudinally within the shaft. One of the pair of balloons is carried on the shaft at a position that is relatively proximal to the other of the pair of balloons. The proximal balloon is typically of greater inflated diameter than the other of the pair of balloons. The proximal balloon typically carries a stent for implantation into a patient.

The stent used in this invention is typically cylindrical in overall shape, and may be of any of the known prior art designs for an expandable stent.

The pair of balloons of the catheter of this invention are typically positioned on the catheter in end-to-end, essentially touching relationship. However, the balloons may be longitudinally spaced from each other if desired, or they may be in relationship where a portion of the balloons overlaps each other to a certain extent, if that is desired. Also, it is preferred for radiopaque marker means to be present on the catheter so that the surgeon can view catheter positioning with a fluoroscope. Typically, the radiopaque marker means are carried adjacent the respective ends of the balloons and may comprise metal rings secured to the catheter.

The catheter of this invention may be constructed in generally conventional manner, for example in a manner similar to catheters as disclosed in Jang U.S. Pat. No. 4,744,366, which catheters disclose a plurality of balloons, and a separate inflation lumen for each of the balloons so that the inflation and the deflation of the respective balloons can be independently controlled.

Thus, an outer, distal balloon of the catheter, which is preferably of smaller inflation size than the proximal balloon, may be inserted into an arterial stenosis in the conventional manner of an angioplasty catheter, and inflated. Then, after full inflation of the distal balloon, it may be deflated, and the catheter of this invention may be advanced with both balloons in deflated condition until the stent carried by the proximal balloon is properly positioned in the stenosis. Then, the proximal balloon, which is typically of larger inflated diameter than the distal balloon, may be inflated to expand the stenosis and the stent into its implanted position within the stenosis, to maintain the patency of the arterial lumen at that point.

DESCRIPTION OF THE DRAWINGS

In the drawings, FIG. 1 is a plan view of the angioplasty catheter of this invention, with the proximal one of a pair of balloons carrying the expansible stent; and FIG. 2 is a perspective view, cut along line 2—2 of FIG. 1, showing the arrangement of lumens in the catheter.

DESCRIPTION OF SPECIFIC EMBODIMENTS

Referring to the drawings, catheter 10 may be manufactured in accordance with conventional technology for the manufacture of angioplasty catheters, with the exception that the catheter carries a pair of longitudinally displaced balloons, with one of the balloons 12 being proximally positioned relative to distal balloon 14. Balloons 12, 14 may be conventionally made of poly(ethylene terephthalate) or the like.

Balloon 12 may be connected to inflation lumen 16 which terminates at its distal end with a branching inflation port 18. Balloon 14 ma be connected to inflation lumen 18, which may be connected to branching inflation port 20.

A third, central lumen 22 is provided to receive a guidewire 24, with lumen 22 extending the entire length of the catheter to permit the catheter to be emplaced in the vascular system of a patient by a conventional guidewire technique.

The main body 26 of the catheter may be made of an extruded tubular plastic material such as polyurethane or soft nylon in accordance with generally conventional manufacturing procedures.

As is conventional, a forward portion of the catheter wall 28 that defines inflation lumen 16 may be cut away to form an open aperture 30 inside of balloon 12. Thus, inflation lumen 16 terminates at a distal position inside of balloon 12 for communication therewith.

Similarly, the wall portion 32 around inflation lumen 18 may be cut away at edge 33 inside of balloon 14 to provide a similar aperture, so that both balloons are independently inflatable and deflatable by pressure or suction applied to the respective ports 18, 20.

Proximal portion 34 of catheter 10, defining the respective ports 18, 20 and also defining axial port 36 for the guidewire, may be molded and then bonded to the extruded catheter portion 26.

Metal marker rings 38 may be placed at the respective ends of the tubular balloons 12, 14, to facilitate the locating of the balloons by means of a fluoroscope within the vascular system of the patient. Additionally, added metal marker rings 40 may be provided adjacent the proximal end of catheter body portion 26.

Preferably, distal balloon 14 may be 15 mm. in length and inflatable to an outer diameter of 1.5 mm. Proximal balloon 12 may in this circumstance have a length which is about 20 mm. in length, having an outer diameter which is variable in various desired catheter sizes between 2.5 mm. and 4.0 mm. Thus, it can be seen that the outer diameter of proximal balloon 12 is larger than distal balloon 14.

In the initial condition prior to use, catheter 10 carries a tubular wire mesh stent 42, which is of known design, and which expands outwardly into a permanently expanded configuration, driven by the expansion of balloon 12. Then, balloon 12 can be deflated once again to leave the stent in its permanently expanded configuration, where it provides a support against collapse of the stenosis site after withdrawal of catheter 10.

Typically, catheter shaft 26 may be about 3½ feet long, with central lumen 22 being capable of receiving a guidewire having a diameter of 0.012–0.014 inch.

If desired, a doubled radiopaque marker ring may be provided on each of the ends of proximal balloon 12 to assist in locating of the stent 42.

The catheter of this invention increases the ease of crossing of a "tight" stenosis, since the stenosis can be penetrated and dilated first with small, distal balloon 14. Then, after such dilation, the catheter is simply advanced further over the guidewire to bring proximal balloon 12 and stent 42 into engagement with the just-dilated stenosis. Because of the dilation, it becomes possible to insert the larger balloon and overlying stent, whereas in many circumstances the insertion of such a balloon with its stent would not be possible without the use of a separate catheter first to dilate the stenosis to a degree to permit insertion of proximal balloon 12 and stent 42.

The catheter of this invention avoids the need for a change of the balloon catheter and the shortening of the time of the procedure. Also, if proximal balloon 12 and stent 42 are on a separate catheter, they cannot be advanced into the stenosis immediately after the dilation making use of balloon 14. The chance of recollapsing of the stenosis while the catheter is being changed is greatly reduced by this invention. Additionally, by this invention not only is the use of a second catheter avoided but the time of the surgical procedure can be significantly shortened.

The catheter of this invention can be used for simple angioplasty without the presence of stent 42, when that is desired.

The above has been offered for illustrative purposes only and is not limited to limit the scope of the invention, which is as defined in the claims below.

That which is claimed is:

1. A balloon catheter which comprises a flexible catheter shaft and at least a pair of inflatable balloons having ends and carried on said catheter shaft, each of said balloons communicating with a separate inflation lumen extending longitudinally within said shaft, one of said pair of balloons being carried on said shaft at a position that is relatively proximal to the other of said pair of balloons, said proximal balloon carrying a stent for implantation into a patient, said stent being spaced from the other of said balloons.

2. The catheter of claim 1 in which said relatively proximal balloon is of greater inflated diameter than the other of said pair of balloons.

3. The catheter of claim 1 in which said relatively proximal and other of said balloons are positioned on the catheter in end-to-end, essentially touching relationship.

4. The catheter of claim 1 in which radiopaque marker means are carried adjacent the ends of said balloons.

5. A balloon catheter which comprises a flexible catheter shaft and at least a pair of inflatable balloons carried on said catheter shaft, each of said balloons communicating with a separate inflation lumen extending longitudinally within said shaft, one of said pair of balloons being carried on said shaft at a position that is relatively proximal to the other of said pair of balloons, said relatively proximal balloon being of greater inflated diameter than the other of said balloons, said relatively proximal balloon carrying a stent for implantation into a patient, said pair of balloons being positioned on the catheter in end-to-end, essentially touching relationship.

6. The catheter of claim 5 in which radiopaque marker means are carried adjacent the ends of said balloons.

7. The method of implanting a stent into an arterial stenosis site of a patient which comprises, inserting into the arterial system of a patient a flexible catheter having a shaft which carries at least a pair of inflatable balloons, each of said balloons communicating with a separate inflation lumen extending longitudinally within said shaft, one of said pair of balloons being carried on the shaft at a position that is relatively proximal to the other of said pair of balloons, the relatively proximal balloon carrying a stent for implantation into a patient; advancing said catheter to cause the other of said balloons to enter the area of said stenosis; inflating the other of said balloons to expand said stenosis and then deflating the other of said balloons; advancing said catheter to place the relatively proximal balloon and stent into the stenosis area; and inflating said relatively proximal balloon to cause said stent to expand into engagement with said stenosis.

8. The method of claim 7 in which said relatively proximal balloon is of greater inflated diameter than the other of said balloons.

9. The method of claim 8 in which said relatively proximal and other of said balloons are positioned on the catheter in end-to-end, essentially touching relationship.

10. The method of claim 9 in which radiopaque marker means are present, and said catheter is manipulated through the method steps while observed through a fluoroscope.

11. The catheter of claim 5 in which said stent is spaced from the other of said balloons.

* * * * *